United States Patent
Fout

(10) Patent No.: US 8,992,451 B2
(45) Date of Patent: Mar. 31, 2015

(54) SHOULDER ORTHOSIS HAVING A SUPPORTIVE STRAPPING SYSTEM

(71) Applicant: Breg, Inc., Carlsbad, CA (US)

(72) Inventor: James M. Fout, Oceanside, CA (US)

(73) Assignee: Breg, Inc., Carlsbad, CA (US)

(*) Notice: Subject to any disclaimer, the term of this patent is extended or adjusted under 35 U.S.C. 154(b) by 4 days.

(21) Appl. No.: 13/831,532

(22) Filed: Mar. 14, 2013

(65) Prior Publication Data

US 2014/0107548 A1    Apr. 17, 2014

Related U.S. Application Data

(62) Division of application No. 13/025,358, filed on Feb. 11, 2011, now Pat. No. 8,414,512.

(51) Int. Cl.
*A61F 5/00* (2006.01)
*A61F 5/37* (2006.01)

(52) U.S. Cl.
CPC ............ *A61F 5/3738* (2013.01); *A61F 5/3753* (2013.01)
USPC ................. 602/4; 602/20; 128/869; 128/878; 224/158

(58) Field of Classification Search
CPC .... A61F 5/3715; A61F 5/3723; A61F 5/3738
USPC .......................... 128/869, 876, 878; 224/158; 5/646–647, 655; 604/4, 20
See application file for complete search history.

(56) References Cited

U.S. PATENT DOCUMENTS

| | | |
|---|---|---|
| 3,103,216 A | 9/1963 | Scott |
| RE30,444 E | 12/1980 | Spann |
| 4,564,008 A | 1/1986 | Donahoo |
| 4,598,701 A | 7/1986 | Schaefer |
| 4,896,660 A | 1/1990 | Scott |
| 5,060,638 A | 10/1991 | Bodine, Jr. |
| 5,086,529 A | 2/1992 | DeGroot |
| 5,236,411 A | 8/1993 | Backman |
| 5,329,941 A * | 7/1994 | Bodine, Jr. .................. 128/845 |

(Continued)

FOREIGN PATENT DOCUMENTS

| | | |
|---|---|---|
| DE | 4134969 A1 | 4/1993 |
| DE | 9402848 | 5/1995 |
| WO | WO2009092348 A1 | 7/2009 |

OTHER PUBLICATIONS

Partial European Search Report; European application No. EP 12 15 4979; published by EPO; May 25, 2012.

(Continued)

*Primary Examiner* — Alireza Nia
*Assistant Examiner* — Camtu Nguyen
(74) *Attorney, Agent, or Firm* — Rodney F. Brown

(57) ABSTRACT

A shoulder orthosis is provided having an arm support and an optional arm spacer connected to the arm support. The arm support includes an arm retainer and a supportive strapping system. One optional arm spacer includes a pair of individual pillows which are attachably combinable with one another at a first face of the first individual pillow and a face of the second individual pillow to form one combined pillow having a first shape. The individual pillows are alternately attachably combinable with one another at a second face of the first individual pillow and the face of the second individual pillow to form another combined pillow having a second shape different from the first shape.

19 Claims, 7 Drawing Sheets

(56) References Cited

U.S. PATENT DOCUMENTS

| | | |
|---|---|---|
| 5,334,132 A | 8/1994 | Burkhead |
| 5,385,536 A | 1/1995 | Burkhead |
| 5,423,333 A | 6/1995 | Jensen |
| 5,464,383 A | 11/1995 | Padden |
| 5,772,617 A | 6/1998 | Lay |
| 6,106,493 A | 8/2000 | Rozell |
| 6,464,656 B1 | 10/2002 | Salvucci |
| 6,659,971 B2 | 12/2003 | Gaylord |
| 6,932,781 B2 | 8/2005 | Itoi |
| 7,189,213 B1 | 3/2007 | Weber |
| 7,244,239 B2 | 7/2007 | Howard |
| 7,300,410 B1 | 11/2007 | Weber |
| 7,563,236 B2 | 7/2009 | Kazmierczak |
| 7,749,179 B2 | 7/2010 | Hargrave |
| 2005/0010147 A1 | 1/2005 | Kazmierczak |
| 2006/0258966 A1 | 11/2006 | Hargrave |

OTHER PUBLICATIONS

Supplemental European Search Report; European application No. 12 15 4979; issued Sep. 10, 2012.
Breg Product Catalog; p. 17; published Aug. 1996.
Breg Product Catalog; published Aug. 2000.
Aircast Arm Immobilizer, www.aircast.com product web page, Feb. 10, 2011.

* cited by examiner

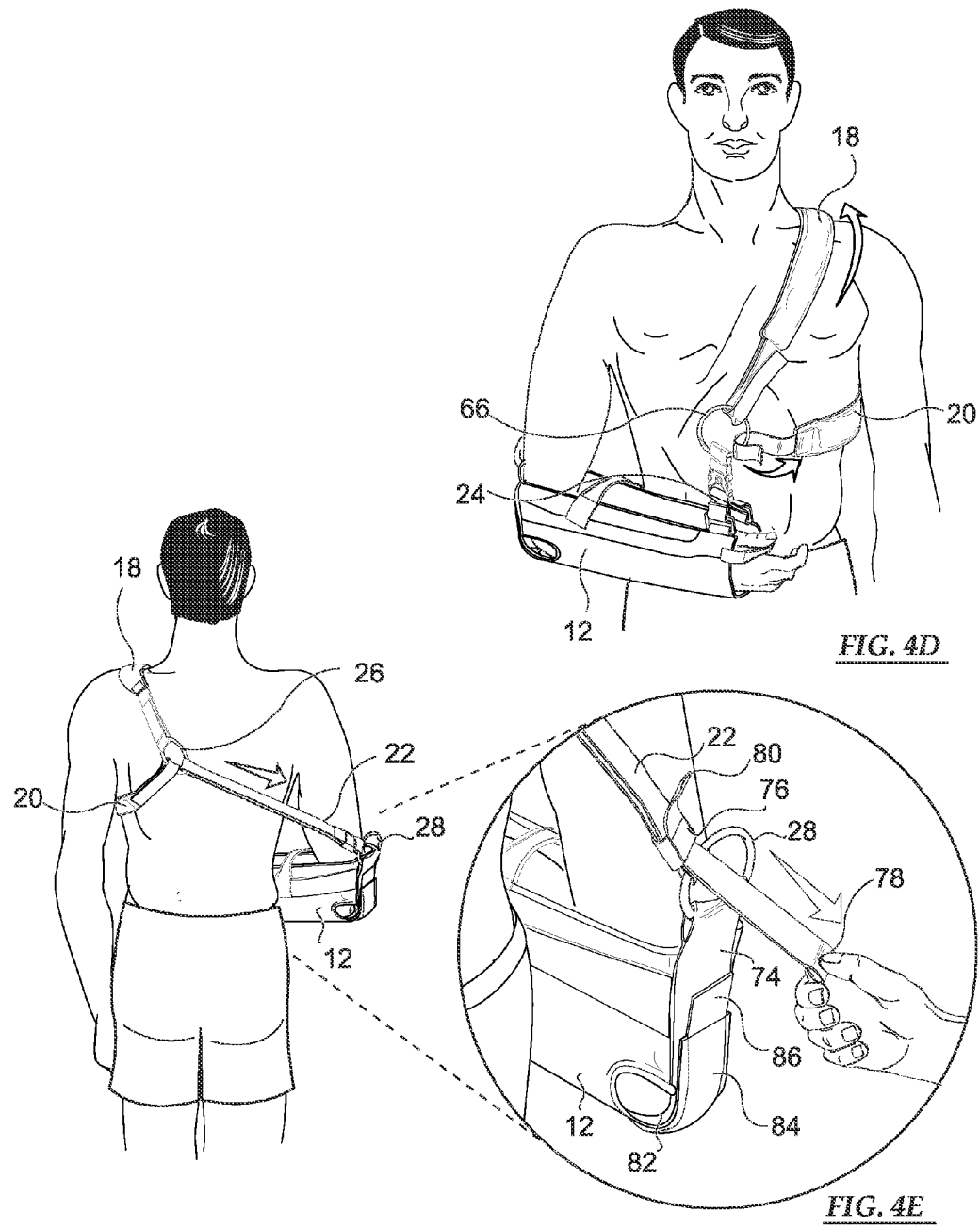

SHOULDER ORTHOSIS HAVING A SUPPORTIVE STRAPPING SYSTEM

BACKGROUND OF THE INVENTION

The present invention relates generally to orthoses, and more particularly to a shoulder orthosis for supporting and stabilizing the shoulder following surgery or injury.

The shoulder is a relatively complex joint of the body which is capable of rotation within multiple planes when the arm is displaced relative to the torso. For example, "external rotation" or "internal rotation" of the shoulder occurs when the forearm is displaced away from or toward the torso while the position of the upper arm is maintained fixed against the side of the torso and the elbow is flexed at 90°. "Abduction" or "adduction" of the shoulder occurs when the upper arm is extended out to the side and is displaced away from or toward the torso. "Flexion" or "extension" of the shoulder occurs when the entire arm is extended out to the front and is displaced toward or away from the torso.

Although the rotational capabilities of the shoulder advantageously enhance the function of the joint, the same expansive rotational capabilities also complicate treatment of the shoulder following injury or surgery. Treatment frequently requires determining a desired optimal treatment position of the shoulder and associated arm, placement of the shoulder and arm in the desired treatment position, and immobilization of the shoulder and arm in the desired treatment position. Such a recuperative treatment is particularly applicable to soft tissue injuries involving damage to one or more connective shoulder ligaments and furthermore is oftentimes the treatment of choice following any number of surgical procedures, including surgery for recurrent posterior subluxation, rotator cuff surgery, humeral head or shaft fracture correction, and the like. Healing occurs inter alia through diminution of inflammation and/or regeneration of muscle tissues, which is promoted by removing stress from the injured or surgically corrected joint.

Support devices for the shoulder, such as orthopedic braces, rigid casts, slings and the like, are commonly employed to perform the above-recited placement and immobilization function with varying degrees of success. For example, commonly-owned U.S. Pat. No. 7,244,239 to Howard, incorporated herein by reference, discloses a shoulder support which includes a forearm wrap, a pair of adjustable straps and a pillow. The wrap and pillow engage the forearm of a patient and the two straps cooperate with the wrap and pillow to suspend the arm at a relatively fixed position of full shoulder flexion while the elbow is flexed at 90°. One strap circles the waist primarily providing a positioning function and only secondarily providing a weight bearing function with respect to the arm and shoulder of the patient. The other strap extends over the shoulder and assumes the primary weight bearing function of the shoulder support. In particular, the shoulder strap transfers the bulk of the arm weight load borne by the shoulder support to the narrow region on the top of the shoulder where the shoulder intersects the neck.

The pillow is cooperatively attachable to the straps and wrap. The pillow, like the waist strap, serves primarily a positioning function with respect to the arm and shoulder of the patient. The pillow is positionable between the elbow and forearm of the patient on one side of the pillow and the torso of the patient on the other side of the pillow to maintain the arm at relatively fixed positions of shoulder abduction/adduction and external/internal rotation. The precise positions of shoulder abduction/adduction and external/internal rotation achieved by the shoulder support of Howard are primarily a function of the specific geometrical configuration and dimensions of the pillow relative to the size and body type of the patient.

The present invention recognizes a need for a shoulder orthosis which more evenly, comfortably and adjustably distributes the arm weight load borne by the shoulder orthosis to the torso of the patient than do shoulder supports disclosed by the prior art. The present invention further recognizes a need for a shoulder orthosis which enables more user adjustability in setting the fixed shoulder treatment position than do shoulder supports disclosed by the prior art. The present invention still further recognizes a need for a shoulder orthosis which enables a user to more easily remove the orthosis and to return the orthosis to its original treatment position with minimal readjustment of the fit than do shoulder supports disclosed by the prior art. Accordingly, among the objects of the present invention are fulfillment of the above-recited needs. These objects and others are accomplished in accordance with the invention described hereafter.

SUMMARY OF THE INVENTION

One characterization of the present invention is a shoulder orthosis comprising an arm retainer, a first strapping segment and a second strapping segment. The arm retainer is configured to engage an arm associated with an affected shoulder opposite an unaffected shoulder. The first strapping segment has a first end and a second end supporting the arm retainer. The first strapping segment has a sufficient length so that it is extendable from its first end across the anterior of the torso, over the unaffected shoulder and across the posterior of the torso to its second end. The second strapping segment has a first end and a second end which are connected to the first strapping segment. The second strapping segment has sufficient length so that it is extendable from its first end across the anterior of the torso, under the arm associated with the unaffected shoulder and across the posterior of the torso to its second end.

In accordance with one embodiment, the first strapping segment includes a first support strap extendable across the anterior of the torso and over the unaffected shoulder and further includes a second support strap connected to the first support strap and extendable across the posterior of the torso. The shoulder orthosis preferably further comprises a first connector and a second connector. The first and second support straps are connected to one another and the second end of the second strap segment is connected to the first strap segment across the first connector. The first end of the second strap segment is connected to the first strap segment across the second connector. The second connector preferably includes a strap loop connected to a releasable buckle.

In accordance with another embodiment, the arm retainer is configured with a front and a rear for engaging the forearm associated with the affected shoulder. The first end of the first strapping segment is connected to the front of the arm retainer and the second end of the first strapping segment is connected to the rear of the arm retainer. The shoulder orthosis preferably further comprises a connector across which the second end of the first strapping segment is connected to the rear of the arm retainer.

Another characterization of the present invention is a shoulder orthosis comprising an arm retainer, a first support strap, a second support strap, a third support strap, a first connector, a second connector and a third connector. The arm retainer is configured to engage an arm associated with an affected shoulder opposite an unaffected shoulder. The first support strap has a sufficient length so that the first support strap is extendable across the anterior of the torso, over the unaffected shoulder and across the posterior of the torso. The second support strap has a sufficient length so that the second support strap is extendable across the anterior of the torso, under the arm associated with the unaffected shoulder and across the posterior of the torso. The third support strap has a sufficient length so that the third support strap is extendable across the posterior of the torso. The first connector connectively engages the first, second and third support straps, the second connector connectively engages the first and second support straps and the arm retainer and the third connector connectively engages the third support strap and arm retainer.

In accordance with one embodiment, the arm retainer is configured with a front and a rear for engaging the forearm associated with the affected shoulder. The first connector is posteriorly positioned to connectively engage the first, second and third support straps. The second connector is anteriorly positioned to connectively engage the first and second support straps and the arm retainer at the front of the arm retainer. The third connector is posteriorly positioned to connectively engage the third support strap and the arm retainer at the rear of the arm retainer. The first and third connectors are preferably strap loops and the second connector preferably includes a strap loop connected to a releasable buckle.

Another characterization of the present invention is a shoulder orthosis comprising an arm support and an arm spacer connected to the arm support. The arm spacer includes a first individual pillow and a second individual pillow. The first individual pillow preferably has an irregular shape. The first and second individual pillows are attachably combinable with one another at a first face of the first individual pillow and a face of the second individual pillow to form a first combined pillow having a first shape. The first and second individual pillows are alternately attachably combinable with one another at a second face of the first individual pillow and the face of the second individual pillow to form a second combined pillow having a second shape different from the first shape. The first combined pillow preferably has a first horizontal width at a point on the first combined pillow alignable with an engagement point on the torso and the second combined pillow preferably has a second horizontal width different from the first horizontal width at a corresponding point on the second combined pillow alignable with the engagement point on the torso.

Another characterization of the present invention is a shoulder orthosis comprising an arm support and an arm spacer connected to the arm support. The arm spacer includes a first individual pillow and a second individual pillow. The first individual pillow preferably has an irregular shape. The first and second individual pillows are attachably combinable with one another at a first face of the first individual pillow and a first face of the second individual pillow to form a combined pillow having a first shape. The first and second individual pillows are alternately attachably combinable with one another at a second face of the first individual pillow and a second face of the second individual pillow to form a combined pillow having a second shape different from the first shape. The first combined pillow preferably has a first horizontal width at a point on the first combined pillow alignable with an engagement point on the torso and the second combined pillow preferably has a second horizontal width different from the first horizontal width at a corresponding point on the second combined pillow alignable with the engagement point on the torso.

Another characterization of the present invention is a shoulder orthosis comprising an arm retainer, a pillow, a first strapping segment and a second strapping segment. The arm retainer is configured to engage an arm associated with an affected shoulder opposite an unaffected shoulder. The pillow is connected to the arm retainer and positionable between the arm associated with the affected shoulder and the torso. The first strapping segment has a first end and a second end supporting the arm retainer and the pillow. The first strapping segment has a sufficient length so that the first strapping segment is extendable from its first end across the anterior of the torso, over the unaffected shoulder and across the posterior of the torso to its second end. The second strapping segment has a first end and a second end connected to the first strapping segment. The second strapping segment has a sufficient length so that the second strapping segment is extendable from its first end across the anterior of the torso, under the arm associated with the unaffected shoulder and across the posterior of the torso to its second end.

In accordance with one embodiment, the pillow is a first individual pillow and the shoulder orthosis further comprises a second individual pillow. The first and second individual pillows are attachably combinable with one another at a first face of the first individual pillow and a face of the second individual pillow to form a first combined pillow positionable between the arm associated with the affected shoulder and the torso which has a first shape. The first and second individual pillows are alternately attachably combinable with one another at a second face of the first individual pillow and the face of the second individual pillow to form a second combined pillow positionable between the arm associated with the affected shoulder and the torso which has a second shape different from the first shape.

In accordance with another embodiment, the first and second individual pillows are attachably combinable with one another at a first face of the first individual pillow and a first face of the second individual pillow to form a combined pillow positionable between the arm associated with the affected shoulder and the torso which has a first shape. The first and second individual pillows are alternately attachably combinable with one another at a second face of the first individual pillow and a second face of the second individual pillow to form a combined pillow positionable between the arm associated with the affected shoulder and the torso which has a second shape different from the first shape.

The present invention will be further understood from the drawings and the following detailed description.

BRIEF DESCRIPTION OF THE DRAWINGS

FIGS. 4A-E show a method for fitting the assembled shoulder orthosis on a patient.

Figure 1:
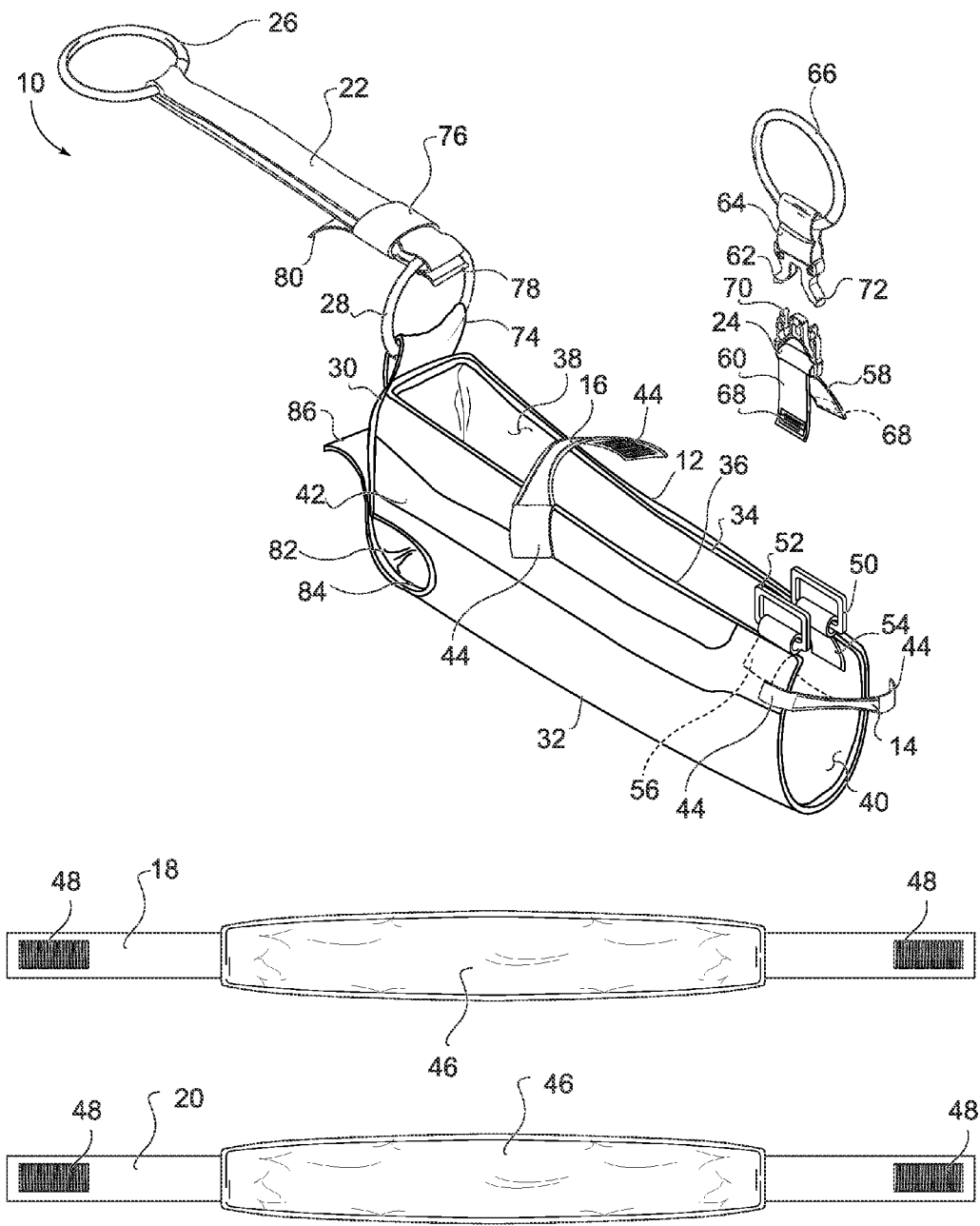
FIG. 1 shows a shoulder orthosis of the present invention in a disassembled state.

Embodiments of the invention are illustrated by way of example and not by way of limitation in the above-recited drawing figures, wherein like reference characters indicate the same or similar elements. It should be noted that common references herein to "an embodiment of the invention", "one embodiment of the invention", "an alternate embodiment of the invention", "a preferred embodiment of the invention", or similar such language are not necessarily references to the same embodiment of the present invention.

DESCRIPTION OF PREFERRED EMBODIMENTS

Referring initially to FIG. 1, a disassembled shoulder orthosis of the present invention is shown and generally designated 10. The shoulder orthosis 10 comprises an arm retainer 12 and a supportive strapping system. The supportive strapping system includes two closure straps 14, 16, three support straps 18, 20, 22, and three connectors 24, 26, 28. Closure strap 14 is termed a front closure strap and closure strap 16 is termed a rear closure strap. Support strap 18 is termed an over-the-shoulder front connective strap insofar as support strap 18 extends over the unaffected shoulder of the user and anteriorly connects to the front of arm retainer 12. Support strap 20 is termed an under-the-arm front connective strap insofar as support strap 20 extends laterally under the arm of the unaffected shoulder of the user and anteriorly connects to the front of arm retainer 12. Support strap 22 is termed a rear connective strap insofar as support strap 22 extends across the back of the user and posteriorly connects to the rear of arm retainer 12.

Connector 24 is termed an anterior multi-strap connector insofar as connector 24 effects anterior connection of the ends of support straps 18, 20 to the front of arm retainer 12. Connector 28 is termed a posterior single-strap connector insofar as connector 28 effects posterior connection of the end of support strap 22 to the rear of arm retainer 12. Connector 26 is termed a posterior multi-strap connector insofar as connector 26 effects the posterior connection of the opposite ends of support straps 18, 20, 22 to one another. One feature distinguishing support straps 18, 20, 22 from connectors 24, 26, 28 is that all support straps 18, 20, 22 have variable lengths which are selectively adjustable by a user, whereas all connectors 24, 26, 28 have fixed non-adjustable lengths.

Arm retainer 12 is preferably a forearm sleeve fabricated from a strong pliant material such as a cloth, cloth/foam laminate, cloth mesh, combinations thereof, or other similarly strong pliant material. Arm retainer 12 may be constructed by preparing a flat cutout of the sleeve from a sheet of the selected pliant material and sewing the cutout into the desired three-dimensional configuration of the sleeve. Arm retainer 12 generally resembles a six-sided polyhedron with rear side 30, bottom side 32, and lateral sides 34, 36 all substantially enclosed and top side 38 and front side 40 substantially open.

Rear side 30 and lateral sides 34, 36 of arm retainer 12 are provided with a fastener 42, which enables the user to releasably fasten closure straps 14, 16 to arm retainer 12 when the shoulder orthosis 10 is assembled in a manner described below. The term "user" is employed herein with reference to either a patient wearing the shoulder orthosis 12 (also termed a wearer), a care provider for the patient, or both. A preferred embodiment of fastener 42 is the hook or loop material of a hook-and-loop fastener commonly known by the trade name VELCRO. The hook or loop material (preferably loop material in this instance) is permanently attached to arm retainer 12 by sewing a continuous strip of the loop material around the outer face of lateral 34, 36 sides and rear side 30 of arm retainer 12.

Closure straps 14, 16 are each relatively short straps formed from a strong pliant material, such as a cloth mesh or other similarly strong pliant material. Both ends of each closure strap 14, 16 are provided with fasteners 44. Each fastener 44 is a tab of hook or loop material which is the opposite material of fastener 42. Fasteners 44 (preferably hook material in this instance) are permanently attached to the closure strap end by sewing or the like. Fasteners 44 enable releasable fastening of closure straps 14, 16 to fastener 42 as described below.

Support straps 18, 20 are essentially identically configured with respect to one another. Each support strap 18, 20 is preferably formed from one or more strong pliant materials resulting in support straps 18, 20 which are not substantially elastically stretchable. The longitudinal midsection 46 of support straps 18, 20 is widened and padded to cushion the torso of the patient when support straps 18, 20 are resting or pressing against the torso during use of the shoulder orthosis 10 as described below. Each support strap 18, 20 is preferably provided with both the hook material and the loop material of a hook-and-loop fastener. In a preferred embodiment, a patch of hook material 48 is permanently attached to the outside face of both ends of each support strap 18, 20 by sewing or the like while the remaining outside face of support strap 18, 20 is preferably continuously covered with, or integrally formed from, loop material. This enables a user to adjust the length of support straps 18, 20 to any desired length shorter than that shown in FIG. 1 as described below.

Connector 24 comprises strap loops 50, 52, connective segments 54, 56, end fasteners 58, 60, a midsection fastener 62, a connective segment 64, and a strap loop 66. Each strap loop 50, 52 has a fully enclosed ring-like configuration, but having a rectangular rather than circular shape. Strap loops 50, 52 are formed from a substantially rigid material such as a rigid metal or plastic. Each connective segment 54, 56 is preferably a short length of strong, pliant, non-stretchable strap material which permanently attaches each strap loop 50, 52 to opposing lateral sides 34, 36 at the top front of arm retainer 12. Permanent attachment is effected by looping each connective segment 54, 56 through its respective strap loop 50, 52 and sewing both ends to arm retainer 12 such that connective segments 54, 56 have a non-adjustable fixed length.

Each end fastener 58, 60 preferably comprises a relatively short length of strong, pliant, non-stretchable strap material having a patch 68 of hook or loop material (preferably hook material in this instance) permanently attached to its outside face by sewing or the like. The remaining outside faces of end fasteners 58, 60 are preferably continuously covered with, or integrally formed from, loop material. Strap loops 50, 52 and end fasteners 58, 60 cooperatively facilitate releasable fastening of connector 24 to arm retainer 12 during assembly of the shoulder orthosis 10 as described below.

Midsection fastener 62 is preferably a manually releasable two-piece buckle commonly known as a side release buckle, which comprises two separate pieces, a lower piece 70 and an upper piece 72, when the buckle is released, but forms a single unitary member when lower and upper pieces 70, 72 are buckled together. Connective segment 64 is preferably a relatively short length of strong, pliant, non-stretchable strap material. Strap loop 66 has a fully enclosed circular ring configuration and is formed from a substantially rigid material such as a rigid metal or plastic.

End fasteners 58, 60 are preferably permanently attached to lower piece 70 of the buckle by looping a single length of strap material through lower piece 70 and sewing it onto itself along a seam immediately adjacent lower piece 70. As such each end fastener 58, 60 has a non-adjustable fixed length and hangs freely below the seam. Connective segment 64 preferably permanently attaches upper piece 72 of the buckle to strap loop 66. One end of connective segment 64 is looped through upper piece 72 and the other end of connective segment 64 is looped through strap loop 66. Both ends of connective segment 64 are sewn onto themselves along a seam between upper piece 72 and strap loop 66 such that connective segment 64 has a non-adjustable fixed length.

Connectors 26, 28 are each a single strap loop having substantially the same construction as strap loop 66. A connective segment 74 is provided having the same or a similar construction to connective segments 54, 56 which preferably permanently attaches connector 28 to arm retainer 12 in substantially the same manner as connective segments 54, 56, but to rear side 30 of arm retainer 12. Connective segment 74 is looped through connector 28 and both ends of connective segment 74 are sewn to rear side 30 of arm retainer 12 such that connective segment 74 has a non-adjustable fixed length.

Support strap 22 is preferably permanently attached to both connector 26 and connector 28. However, permanent attachment of support strap 22 to connectors 26, 28 is effected in a manner which enables the user to adjust the length of support strap 22. In particular, permanent, yet adjustable, attachment is effected by providing a strap keeper 76 which encircles support strap 22. One end of support strap 22 is permanently attached to keeper 76, preferably by sewing. The remaining free end of support strap 22 is displaced in a first direction away from keeper 76 to connector 28, looped through connector 28, and displaced back in a second opposite direction toward keeper 76 thereby overlapping itself. The free end is passed through keeper 76 in the second direction, looped through connector 26 and displaced in the first direction again away from connector 26, thereby overlapping itself. The free end is finally passed through keeper 76 one last time in the first direction. A nub 78 is then formed on the free end of support strap 22, which extends from keeper 76 in the first direction, by doubling the free end one or more times back over itself and sewing the doubled over segments together. Nub 78 is sized to prevent the free end of support strap 22 from passing back through keeper 76 in the second direction.

Support strap 22 is preferably formed from one or more strong pliant materials which are not substantially elastically stretchable, e.g., the same material as support straps 18, 20. Support strap 22 is preferably continuously covered with, or integrally formed from, a hook or loop material (preferably loop material in this instance) in the manner of support straps 18, 20. A fastener 80, preferably a tab of the hook or loop material (more preferably hook material in this instance) which is opposite the material of support strap 22, is permanently attached to keeper 76 by sewing or the like and extends away from keeper 76 for releasable fastening to the face of support strap 22.

Fastener 80, in cooperation with keeper 76, enables the user to selectively set the length of support strap 22. In particular, the user decreases the length of support strap 22 by releasing fastener 80 from the face of support strap 22 adjacent to keeper 76 and displacing nub 78 away from keeper 76 in the first direction, thereby drawing a length of support strap 22 behind nub 78 through keeper 76 in the first direction and effectively drawing connectors 26, 28 closer together. Once the desired decreased strap length is reached, the user refastens fastener 80 to the face of support strap 22 adjacent to keeper 76. The user increases the length of support strap 22 by releasing fastener 80 from the face of support strap 22 adjacent to keeper 76 and displacing nub 78 back toward keeper 76 in the second direction, thereby drawing a length of support strap 22 back through keeper 76 in the first direction and effectively distancing connectors 26, 28 from one another. Once the desired increased strap length is reached the user refastens fastener 80 to the face of support strap 22 adjacent to keeper 76.

Figure 2:
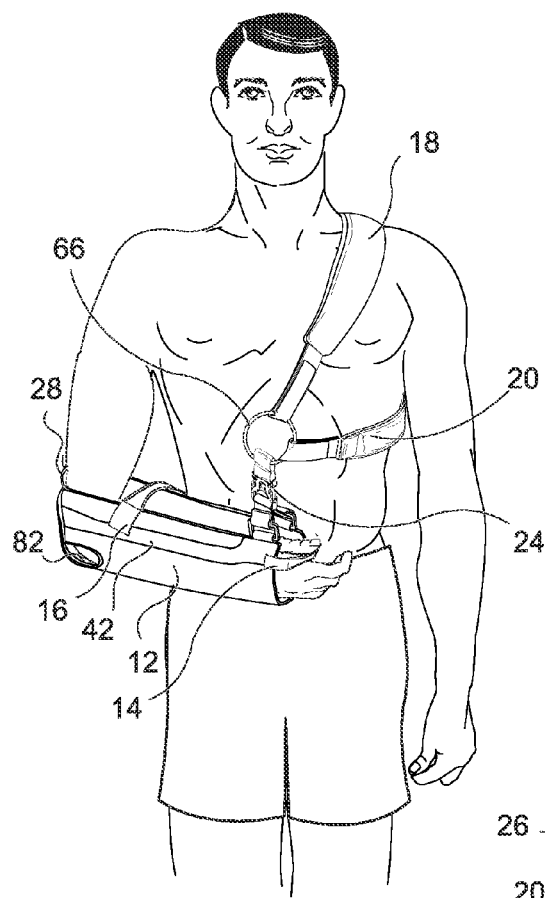
FIG. 2 is a front view of the assembled shoulder orthosis of FIG. 1 worn by a patient.
Figure 3:
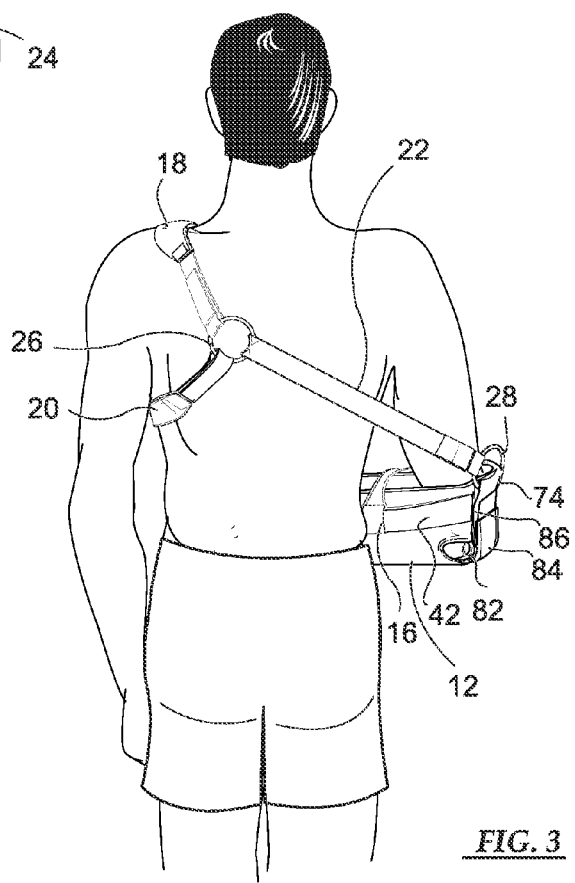
FIG. 3 is a rear view of the assembled shoulder orthosis of FIG. 1 worn by a patient.

FIGS. 2 and 3 show the assembled shoulder orthosis 10 worn by a patient for effective support and stabilization of the right shoulder of the patient. It is readily apparent to one of ordinary skill in the art that it is also within the scope of the present invention to adapt the shoulder orthosis 10 for effective support and stabilization of the left shoulder. The shoulder orthosis 10 is assembled from its disassembled state shown in FIG. 1 to its assembled state shown in FIGS. 2 and 3 by looping an end of support strap 18 and an end of support strap 20 through connector 26 and doubling each of the ends back over itself a relatively short distance. The ends are releasably fastened back onto themselves by means of fasteners 48, thereby releasably connecting support straps 18, 20 to support strap 22, which in turn is permanently connected to the rear of arm retainer 12 by means of connector 28. The remaining free end of support strap 18 and remaining free end of support strap 20 are likewise looped through strap loop 66 of connector 24, similarly doubled back over themselves and releasably fastened to themselves with fasteners 48, thereby releasably connecting support straps 18, 20 to upper piece 72 of buckle 62 on connector 24. As a result, each support strap 18, 20 has been adjusted to an unfitted strap length which is preferably an increased unfitted strap length. Support strap 22 is also adjusted to an unfitted strap length, which is preferably an increased unfitted strap length, in a manner described above specific to support strap 22. Assembly of the shoulder orthosis 10 continues by releasably fastening end fasteners 58, 60 of connector 28 to their corresponding strap loops 50, 52 which are attached to opposite lateral sides 34, 36 of arm retainer 12 while lower piece 70 of buckle 62 remains uncoupled from upper piece 62.

Figure 4A:
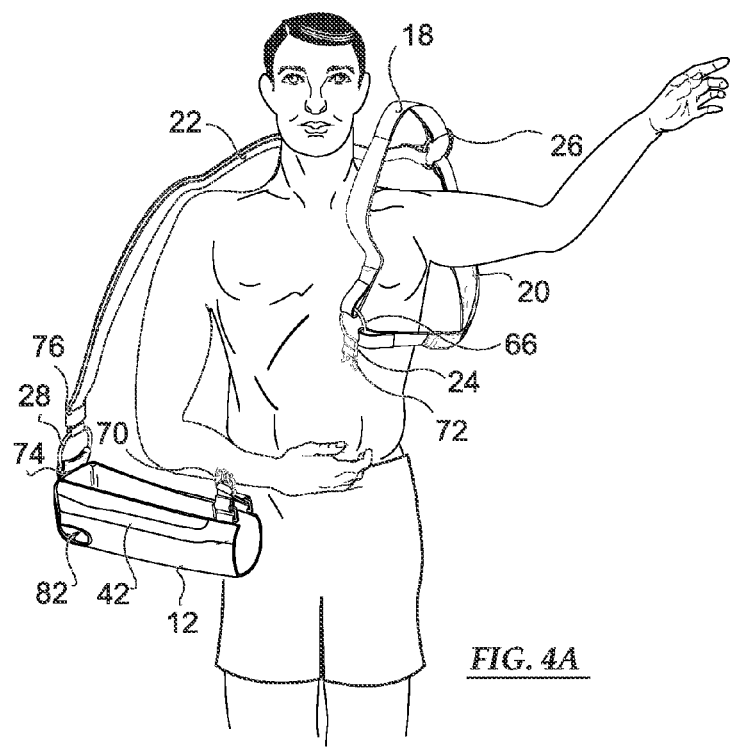

Once the shoulder orthosis 10 is in a partially assembled state as shown in FIG. 4A, it is in a condition for fitting on a patient. A method for properly fitting the partially assembled shoulder orthosis 10 on a patient is described below with reference to FIGS. 4A-E. The method is initiated as shown in FIG. 4A by extending the arm associated with the patient's unaffected shoulder (the left arm in the present illustration) away from the body while the arm associated with the affected shoulder on the opposite side of the body (the right arm in the present illustration) is positioned at the patient's side, if desired, in a relaxed state.

The closed loop formed by the support straps 18, 20, connector 26, and strap loop 66 of connector 24 is passed around the extended arm toward the patient's torso. Support strap 18 is positioned above the arm such that support strap 18 extends across both the anterior and posterior of the torso and extends therebetween over the unaffected shoulder. Support strap 20 is positioned below the arm such that support strap 20 likewise extends across both the anterior and posterior of the torso, but extends therebetween laterally beneath the unaffected shoulder. Mounting the strapping system on the patient is completed by extending support strap 22 across the posterior of the torso. As such, the instant strapping system emulates essentially two strapping segments. One strapping segment extends over the shoulder and connects to the front and back of arm retainer 12 as accomplished by support straps 18, 22 in combination. The other strapping segment extends under the shoulder and connects posteriorly and anteriorly to the first strapping segment as accomplished by support strap 20.

Figure 4B:
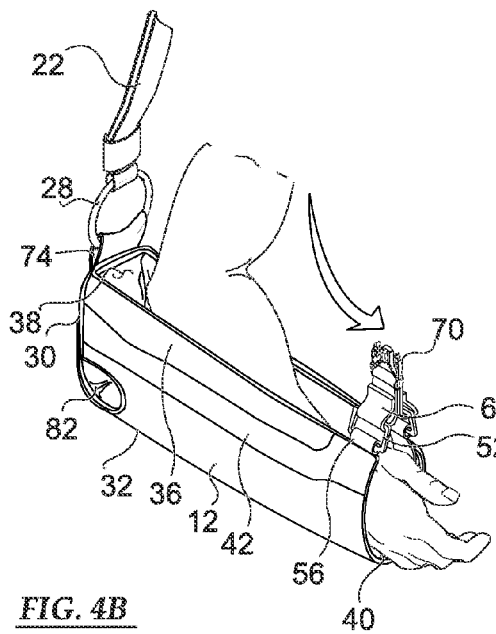

Once the strapping system is mounted on the patient, the extended arm may be lowered back against the patient's body. Arm retainer 12 is manually positioned adjacent to the arm which is associated with the affected shoulder and fitting the shoulder orthosis 10 on the patient continues by placing the forearm associated with the affected shoulder in arm retainer 12. In particular, the patient's hand associated with the affected shoulder is slipped diagonally into open top side 38 of arm retainer 12 near its midpoint and extended diagonally forward under end fasteners 58, 60 as shown in FIG. 4B until the forearm is cradled in arm retainer 12. As such, the forearm engages arm retainer along enclosed bottom side 32 and lateral sides 34, 36, the elbow engages arm retainer at the intersection of rear side 30 and bottom side 32 and the hand extends out open front side 40 of arm retainer 12.

An opening 82 may be provided in arm retainer 12 at the intersection of rear side 30 and bottom side 32 where the elbow engages arm retainer 12. The elbow opening 82 can be selectively maintained opened or closed by means of a closure strip 84 integrally formed with the arm retainer 12 as shown in FIG. 1 and shown more fully in FIG. 4E. The end of closure strip 84 has a fastener 86 which is preferably a tab of hook or loop material (more preferably hook material in this instance) opposite the material of fastener 42. Fastener 86 is permanently attached to the closure strip end by sewing or the like and enables releasable fastening of closure strip 84 to fastener 42, thereby covering opening 82 and correspondingly covering the elbow. Conversely, releasably unfastening closure strip 84 from fastener 42 uncovers opening 82 and correspondingly uncovers the elbow. This may be desirable when a wound or any other condition is present on the elbow which would be irritated by contact with arm retainer 12.

Figure 4C:
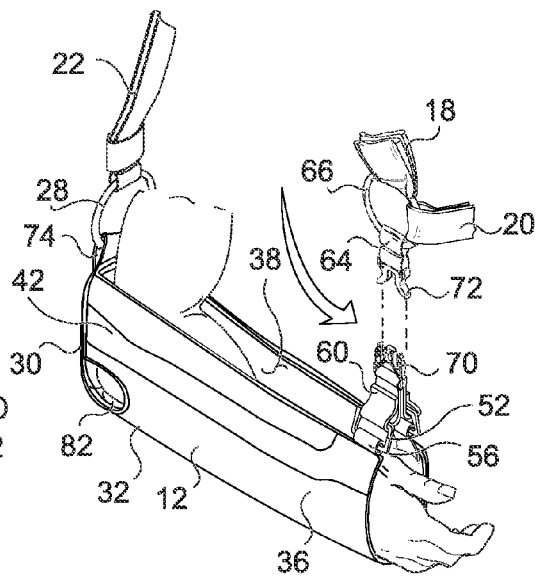

In any case, after the forearm is cradled in arm retainer 12 lower and upper pieces 70, 72 of buckle 62 are coupled together as shown in FIG. 4C, thereby releasably connecting support straps 18, 20 to the front of arm retainer 12 by means of connector 24. With support straps 18, 20, 22 connected to the front and rear of arm retainer 12, support straps 18, 20, 22 desirably support the load of arm retainer 12 and the arm cradled therein. Fitting the shoulder orthosis 10 on the patient is completed with reference to FIGS. 4D and E by adjusting the lengths of support straps 18, 20, 22 from the unfitted strap lengths of FIG. 4A to fitted strap lengths.

The fitted strap lengths are typically, but not necessarily, decreased fitted strap lengths relative to the preferred increased unfitted strap lengths of support straps 18, 20, 22 described above. In any case, with specific reference to FIG. 4D, decreasing the strap length of support strap 18, 20 from the unfitted strap length to a decreased fitted strap length is effected by releasing fastener 48 on the strap end at the front of the patient proximal to strap loop 66, pulling on the strap end away from strap loop 66 until fastener 48 aligns with a point on support strap 18, 20 corresponding to the desired decreased fitted strap length and refastening fastener 48 to support strap 18, 20 at that point. Conversely, increasing the strap length of support strap 18, 20 from the unfitted strap length to an increased fitted strap length, if necessary, is effected by releasing fastener 48 on the strap end at the front of the patient proximal to strap loop 66, drawing the strap end toward strap loop 66 until fastener 48 aligns with a point on support strap 18, 20 corresponding to the desired increased fitted strap length and refastening fastener 48 to support strap 18, 20 at that point.

With specific reference to FIG. 4E, decreasing the strap length of support strap 22 from the unfitted strap length to a decreased fitted strap length is effected by releasing fastener 80 from support strap 22 and pulling nub 78 away from keeper 76 in the first direction until a point on support strap 22 corresponding to the desired decreased fitted strap length aligns with fastener 80 and refastening fastener 80 to support strap 22 at that point. Conversely, increasing the strap length of support strap 22 from the unfitted strap length to an increased fitted strap length, if necessary, is effected by releasing fastener 80 from support strap 22 and pushing nub 78 toward keeper 76 in the second direction until a point on support strap 22 corresponding to the desired increased fitted strap length aligns with fastener 80 and refastening fastener 80 to support strap 22 at that point.

It is noted that the fitted strap lengths of support straps 18, 20, 22 are selected by the user in accordance with the instant shoulder orthosis fitting method to optimally minimize the weight-bearing load on the affected shoulder. As such, the properly fitted shoulder orthosis 10 preferably distributes most, if not all, of the weight of the arm associated with the affected shoulder to the side of the patient's torso opposite the affected shoulder. The properly fitted shoulder orthosis 10 also preferably distributes at least a substantial portion of the weight of the arm associated with the affected shoulder away from the intersection of the neck and the unaffected shoulder on opposite the side of the patient's torso to a region on the shoulder away from the neck, thereby enhancing the comfort of the patient.

After the shoulder orthosis 10 has been properly fitted on the patient, assembly of the shoulder orthosis 10 is completed by releasably fastening closure straps 14, 16 to the front and rear of arm retainer 12, respectively, as shown in FIGS. 2 and 3. One end of closure strap 16 is releasably fastened by means of fastener 44 to fastener 42 on one lateral side 32 or 34 of arm retainer 12 proximal to rear side 30 and immediately in front of the patient's upper arm extending upwardly out of arm retainer 12. The other end of closure strap 16 is pulled comfortably taut over open top side 38 of arm retainer 12 and fastened by means of other fastener 44 to fastener 42 on the opposite lateral side 32 or 34 of arm retainer 12, thereby substantially closing open top side 38 at that point. Similarly, one end of closure strap 14 is releasably fastened by means of fastener 44 to fastener 42 on one lateral side 32 or 34 of arm retainer 12, but proximal to open front side 40 of arm retainer 12 and adjacent to the opening between in the patient's thumb and index finger extending out of arm retainer 12. The other end of closure strap 14 is pulled comfortably taut over open front side 40 of arm retainer 12, drawn between the thumb/index finger opening and fastened by means of other fastener 44 to fastener 42 on the opposite lateral side 32 or 34 of arm retainer 12, thereby substantially closing open front side 40 at that point. As such, closure straps 14, 16 effectively secure the patient's forearm within arm retainer 12.

Advantageous features of the shoulder orthosis 10 include the ability to remove it from its operative fitted position on the patient without requiring the user to substantially disassemble of the shoulder orthosis 10, without requiring the user to change the length of any support straps 18, 20, 22 from their adjusted fitted strap lengths, or without requiring the patient to substantially displace the arm associated with the affected shoulder away from the patient's body and correspondingly without requiring the patient to substantially rotate the affected shoulder. Removal of the shoulder orthosis 10 from its fitted position on the patient is readily effected by performing the steps of FIGS. 4A-C in reverse after releasing closure straps 14, 16 from arm retainer 12. In particular, removal is effected by uncoupling lower and upper pieces 70, 72 (the reverse of FIG. 4C), withdrawing the forearm from arm retainer 12 (the reverse of FIG. 4B) and passing the closed loop formed by the support straps 18, 20, connector 26, and strap loop 66 back over the extended arm associated with the unaffected shoulder away from the patient's torso (the reverse of FIG. 4A). If the user subsequently desires to operatively reposition the shoulder orthosis 10 on the patient, it is apparent that the user need only repeat the steps of FIGS. 4A-C and refasten closure straps 14, 16. It is unnecessary to readjust any of the support strap lengths in the manner of FIGS. 4D and 4E to restore the proper fit when removing and repositioning the shoulder orthosis 10.

The shoulder orthosis 10 may also optionally comprise a shoulder positioning pillow system which is incorporated into the shoulder orthosis 10 in cooperative association with arm retainer 12 and the supportive strapping system described above with reference to FIGS. 1-4. The shoulder positioning pillow system functions as an arm spacer positionable between the arm retainer 12, intervening forearm and torso of a user to distance the forearm from the torso and position the arm at an angle which effects a desired treatment position of the shoulder in a manner described below with reference to FIGS. 5-8. According to one embodiment shown in FIG. 6, the shoulder positioning pillow system has one individual shoulder positioning pillow 90 which alone functions as the arm spacer. According to another embodiment, the shoulder positioning pillow system is a modular multi-pillow system having two or more individual pillows which in combination function as the arm spacer. An exemplary embodiment of a modular multi-pillow system shown in FIG. 5 has two individual pillows 90, 92. When individual pillows 90, 92 are combined in releasable attachment as shown in FIGS. 7 and 8, individual pillows 90, 92 form a single pillow termed a combined shoulder positioning pillow which functions as the arm spacer.

Each individual pillow 90, 92 preferably has essentially the same configuration and construction as the other. Accordingly, the description of individual pillow 90 set forth below applies likewise to individual pillow 92. Furthermore, it is understood that pillow elements which are visible on pillow 90 in FIGS. 5-8, but which are obscured on pillow 92 or vice versa due to the particular view of a given figure are nevertheless present on both pillows 90, 92.

Figure 5:
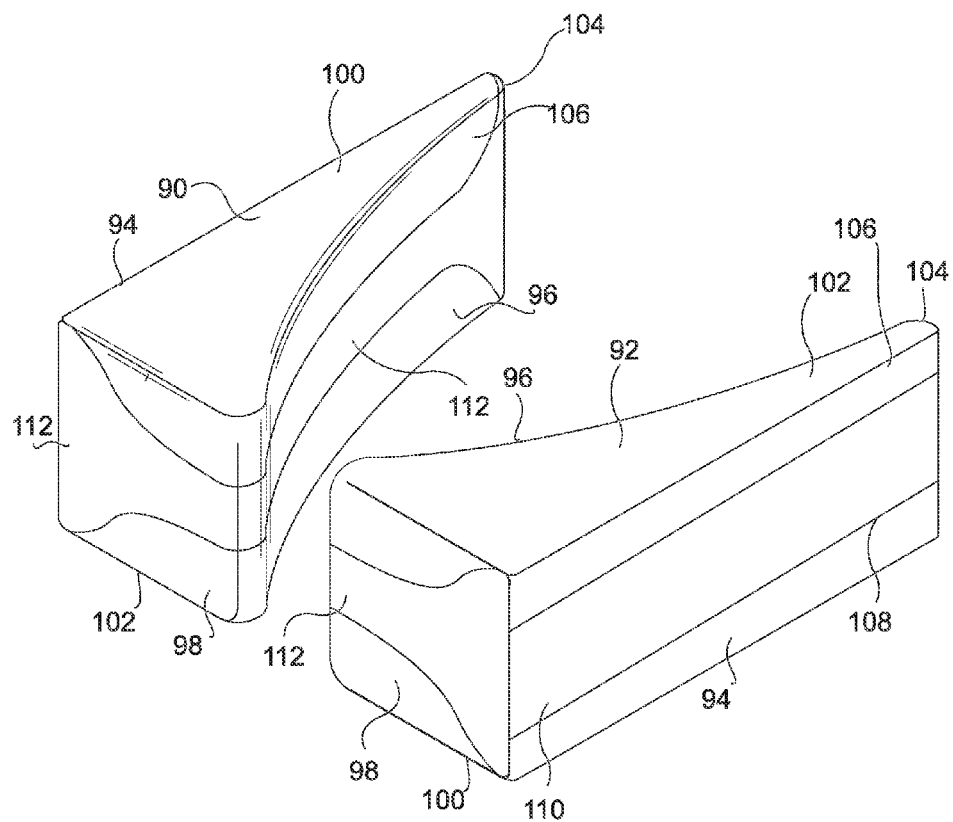
FIG. 5 is a perspective view of a shoulder positioning pillow system which is optionally employed with the shoulder orthosis of FIG. 1.
Figure 5:
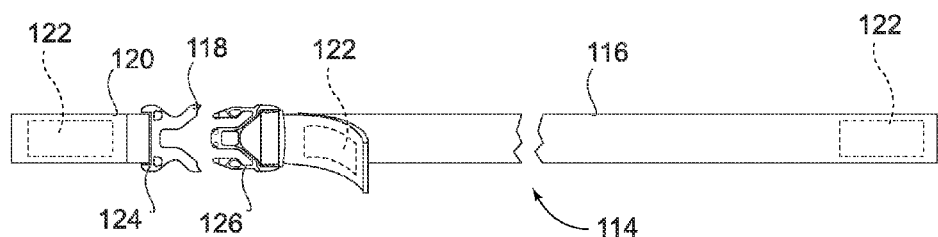

Referring to FIG. 5, pillow 90 preferably has a wedge configuration with five faces, i.e., three substantially vertically-oriented faces 94, 96, 98 and two substantially horizontally-oriented faces 100, 102. The terms "vertical" and "horizontal" are used in the present context with reference to the orientation of faces 94, 96, 98, 100, 102 when pillow 90 is operatively mounted on a patient, as will be described below, in cooperative association with the other components of the shoulder orthosis 10 described above. As is characteristic of a wedge configuration, two vertical faces 94, 96 of pillow 90 are preferably elongate and converge at one of their aligned ends to a common edge of intersection 104 which is tapered at an acute angle. Two vertical faces 94, 96 diverge at their opposite aligned ends to define vertical face 98 which extends between the two divergent edges of vertical faces 94, 96 and is relatively shorter in length than elongate vertical faces 94, 96. Vertical face 98 intersects with vertical face 94 preferably at an essentially right angle and intersects with vertical face 96 at an acute angle which is preferably substantially greater than the acute angle of edge 104.

Horizontal faces 100, 102 are preferably substantially planar and essentially parallel to one another while being essentially normal to vertical faces 94, 96, 98. Vertical faces 94, 98 are likewise preferably substantially planar and vertical face 94 has a length which is preferably approximately equal to the length of arm retainer 12 and correspondingly approximately equal to the length of a typical patient's forearm. Vertical face 96 is preferably at least somewhat arcuate and more preferably has a relatively shallow arc and correspondingly a relatively large radius of curvature to approximately conform to the shallow arcuate contour along an anterior surface of the torso of a patient at or near the waist. As such, vertical face 96, in gross, approximates a planar rectangle and horizontal faces 100, 102 approximate a planar right triangle with the top edge of vertical face 96 defining the hypotenuse of the triangle.

Pillow 90 is preferably constructed from a single molded or cut-out piece of shaped foam (not shown) having the above-described configuration. Although the foam of pillow 90 is compressible, it is nevertheless relatively firm so that pillow 90 does not substantially deform when contacted by the forearm during normal use of the shoulder orthosis 10. However, arcuate vertical face 96 of pillow 92 may deformably flatten somewhat when pillows 90, 92 are pressed against one another to form the combined shoulder positioning pillow as described below. The entirety of the foam piece is preferably enclosed in a shell 106 which is constructed from a thin high-strength pliant material, such as a cloth, cloth/foam laminate, cloth mesh, or combinations thereof. Shell 106 can serve multiple functions, e.g., protecting the foam from abrasion or other external degradation, enhancing the comfort of the patient, reducing the surface friction coefficient of pillow 90 and/or providing a substrate or platform for attaching fasteners or other accessories to the face of pillow 90.

Shell 106 is preferably constructed by preparing a flat cutout of the shell from a sheet of the selected pliant material and sewing the cutout into the desired three-dimensional configuration of the shell, but leaving a flap 108 in shell 106 through which to insert the foam piece for final assembly of pillow 90. A fastener such as a hook-and-loop fastener (not shown) can be provided to internally fasten flap 108 closed during use of pillow 90. Vertical face 94 is provided with a fastener 110 and vertical faces 96, 98 are provided with a fastener 112, which in combination enable the user to releasably fasten pillow 90 to arm retainer 12 of the shoulder orthosis 10 or releasably fasten individual pillows 90, 92 to one another when forming any one of the various alternate configurations of the combined shoulder positioning pillow as described below. A preferred embodiment of fastener 110 is the hook or loop material of a hook-and-loop fastener. The hook or loop material of fastener 110 (preferably hook material in this instance) is permanently attached to vertical face 94 by sewing a continuous strip of the hook material thereto. A preferred embodiment of fastener 112 is likewise the hook or loop material, but the opposite material of fastener 110. The hook or loop material of fastener 112 (preferably loop material in this instance) is permanently attached to vertical faces 96, 98 by sewing a continuous strip of the loop material thereto.

The shoulder positioning pillow system preferably further comprises a waist belt 114 as an accessory associated with pillow 90. Waist belt 114 comprises a waist strap 116, a midsection fastener 118 and a connective segment 120. Waist strap 116 and connective segment 120 are preferably formed from one or more strong pliant materials which are not substantially elastically stretchable, e.g., the same material as support straps 18, 20, 22. Waist strap 116 and connective segment 120 are preferably continuously covered with, or integrally formed from, a hook or loop material (preferably loop material in this instance) in the manner of support straps 18, 20, 22. Three fasteners 122, each preferably a patch of the hook or loop material (more preferably hook material in this instance) which is opposite the material of waist strap 116 and connective segment 120 are permanently attached to waist belt 114 by sewing or the like. One fastener 122 is attached to the inside face at one end of relatively short connective segment 120, another fastener 122 is attached to the inside face at one end of relatively long waist strap 116 and another fastener 122 is attached to the outside face at the opposite end of waist strap 116.

Midsection fastener 118 is preferably a two-piece side release buckle which is substantially the same as midsection fastener 62. Connective segment 120 is preferably permanently attached to one piece 124 of the buckle by looping one end of connective segment 120 through piece 124 and sewing it back onto itself immediately adjacent to piece 124 such that connective segment 120 has a non-adjustable fixed length. Waist strap 116 is preferably slidably attached to the other piece 126 of the buckle by looping the end of waist strap 116 having fastener 122 attached to the outside face thereof through piece 126 and doubling the end back over itself so that both fasteners 122 on waist strap 116 are facing the same direction. This configuration enables the user to releasably adjust the length of waist strap 116. The user decreases the length of waist by releasing fastener 122 on the end of waist strap 116 looped through piece 126, pulling the strap end away from piece 126 until fastener 122 aligns with a point on waist strap 116 corresponding to the desired decreased strap length and refastening fastener 122 to waist strap 116 at that point. Conversely, the user increases the length of waist strap 116 by releasing fastener 122 on the end of waist strap 116 looped through piece 126, pulling the strap end toward piece 126 until fastener 122 aligns with a point on waist strap 116 corresponding to the desired increased strap length and refastening fastener 122 to waist strap 116 at that point.

Waist belt 114 is preferably cooperatively assembled with pillow 90 by releasably fastening fastener 122 of connective segment 120 to fastener 112 on vertical face 98 while piece 124 of buckle remains uncoupled from piece 126. As such, piece 124 is substantially positioned at the intersecting edge of vertical faces 96 and 98 of pillow 90. Waist strap 116 is set at an unfitted strap length in a manner described above and the free end of waist strap 116 not looped through piece 126 is aligned with flap 108. The free end of waist strap 116 is tucked beneath flap 108 and releasably fastened to the inside of flap 108 by means of fastener 122 on the strap end such that piece 126 of the buckle is directed toward edge 104 of pillow 90 and away from vertical face 98.

Once the waist belt 114 and pillow 90 are assembled, the shoulder orthosis 10 including the shoulder positioning pillow system is in a condition for mounting on a patient. A method for mounting the shoulder orthosis 10, which includes the shoulder positioning pillow system, on a patient is described below with reference to FIGS. 6A-D. The shoulder positioning pillow system shown in FIG. 6D has only one individual shoulder positioning pillow which is configured to maintain the affected shoulder of a patient in a desired treatment position. The instant shoulder treatment position is termed a 45° neutral treatment position. When the shoulder is in the 45° neutral treatment position, the forearm is rotated to a 45° external rotation angle while the upper arm is at a 0° (neutral) abduction angle.

Figure 6A:
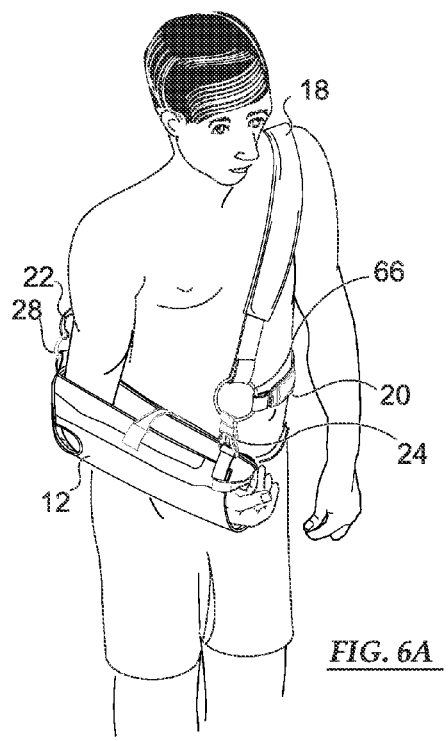
FIGS. 6A-D show a method for mounting the shoulder orthosis, which includes a configuration of the pillow system of FIG. 5, on a patient to maintain the shoulder in a 45° neutral treatment position.
Figure 6B:
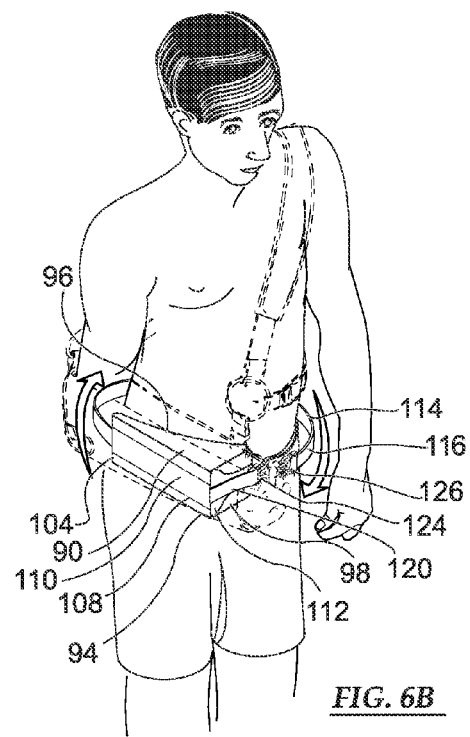
Figure 6C:
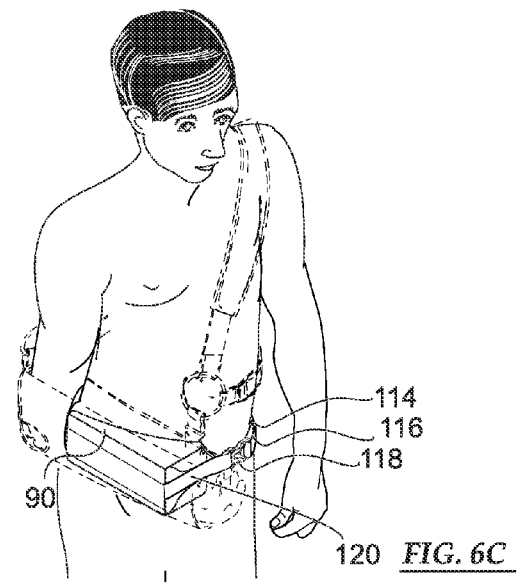
Figure 6D:
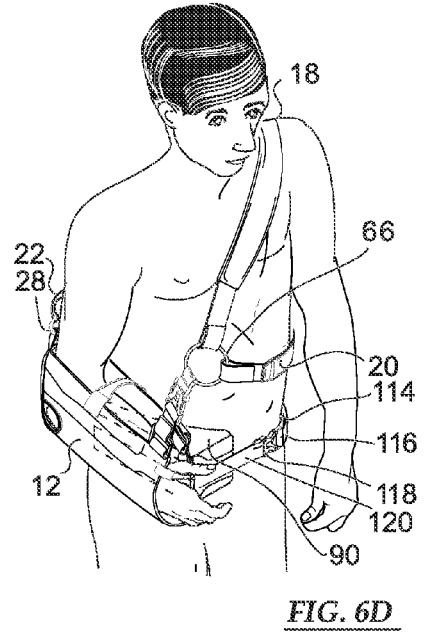

In accordance with the present method, arm retainer 12 and the strapping system are mounted on the patient as described above and shown in FIG. 6A. Vertical face 96 is positioned in engagement with the patient's anterior torso at or near the waist with edge 104 directed posteriorly and vertical face 98 directed anteriorly. Pillow 90 having waist belt 114 assembled thereon is positioned in engagement with arm retainer 12 as shown in FIG. 6B. More particularly, vertical face 94 is releasably fastened to lateral side 34 by means of fasteners 110 and 42, respectively. Waist strap 116 is wrapped around the waist of the patient and pieces 124, 126 are buckled together as shown in FIGS. 6B and 6C. Mounting is completed by snugly fitting waist belt 114 to the waist as described above.

In accordance with an alternate method, pillow 90 is fastened to arm retainer 12 before mounting arm retainer 12 and the strapping system on the patient. In all other respects, this alternate mounting method is essentially the same as described above. In either case, by posteriorly positioning the narrowest segment of individual shoulder positioning pillow 90 at edge 104 adjacent to the elbow, the shoulder orthosis 10 having the instant individual pillow configuration imposes a neutral treatment position of 0° on the shoulder with respect to abduction. Conversely by anteriorly positioning the widest segment of pillow 90 at vertical face 98 adjacent to the wrist, the shoulder orthosis 10 having the instant individual pillow configuration imposes an angular treatment position of 45° with respect to external rotation.

Another method for mounting the shoulder orthosis 10, which includes an alternate shoulder positioning pillow system, is described below with reference to FIGS. 7A and 7B. The present method is essentially the same as described above with reference to FIGS. 6A-D except that a combined pillow made up of two releasably attached individual pillows is employed as the shoulder positioning pillow system in the instant method. The individual pillows of the combined pillow are alternately aligned in different pillow alignments resulting in different configurations of the combined pillow which correspondingly impose different treatment positions on the affected shoulder. One configuration of the combined pillow is an enhanced shoulder rotation configuration having a corresponding pillow alignment. Another configuration of the combined pillow is an enhanced shoulder abduction configuration having a different corresponding pillow alignment. In accordance with an embodiment of the enhanced shoulder rotation configuration, the combined pillow is configured to maintain the affected shoulder of a patient in a 90° neutral treatment position. The combined pillow is assembled by positioning pillow 92 to the outside of pillow 90 with vertical face 98 of pillow 92 positioned adjacent vertical face 98 of pillow 90 and edge 104 of pillow 92 positioned adjacent edge 104 of pillow 90. Vertical face 96 of pillow 92 is pressed against vertical face 94 of pillow 90 causing fastener 112 of pillow 92 to engage fastener 110 of pillow 90 and maintain the instant combined pillow configuration. Waist belt 114 is maintained assembled on pillow 90 and fitted in substantially the same manner as described above with respect to the method employing the single individual shoulder positioning pillow.

Vertical face 96 of pillow 90 is positioned in engagement with the patient's anterior torso at or near the waist with edges 104 of both pillows 90 and 92 directed posteriorly and vertical faces 98 of both pillows 90 and 92 directed anteriorly. Vertical face 94 of pillow 92 is positioned in engagement with arm retainer 12 and is releasably fastened to lateral side 34 by means of fasteners 110 and 42, respectively. The instant configuration of the combined pillow does not significantly increase the overall horizontal pillow width relative to FIG. 6D at the segment corresponding to edges 104, which is termed the posterior width dimension of the combined pillow in the enhanced shoulder rotation configuration. Accordingly, by posteriorly positioning the narrowest segment of the combined pillow adjacent to the elbow, the shoulder orthosis 10 having the instant combined pillow configuration continues to impose a neutral treatment position of 0° on the shoulder with respect to abduction. However, the instant combined pillow configuration effectively doubles the overall horizontal pillow width relative to FIG. 6D at the segment corresponding to vertical faces 98, which is correspondingly termed the anterior width dimension of the combined pillow in the enhanced shoulder rotation configuration. As such, it is apparent from the description above and FIG. 7B that the posterior width dimension is substantially less than the anterior width dimension of the combined pillow in the enhanced shoulder rotation configuration. Accordingly, by anteriorly positioning the widest segment of the combined pillow adjacent to the wrist, the shoulder orthosis 10 having the instant combined pillow configuration imposes an increased angular treatment position of 90° with respect to external rotation.

Figure 7A:
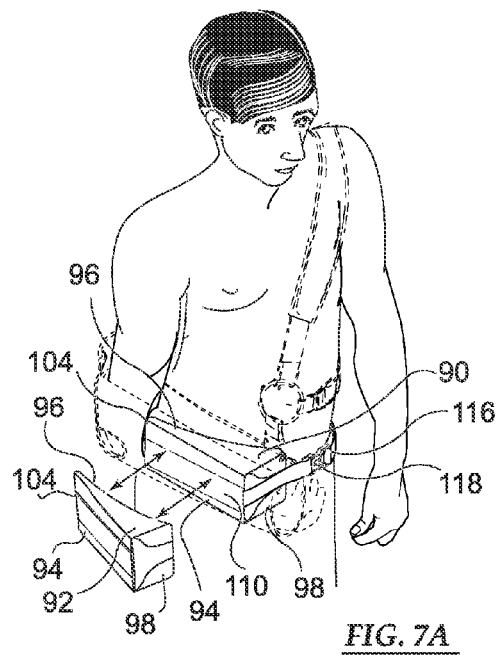
FIGS. 7A and 7B show a method for mounting the shoulder orthosis, which includes an alternate configuration of the pillow system of FIG. 5, on a patient to maintain the shoulder in a 90° neutral treatment position.
Figure 7B:
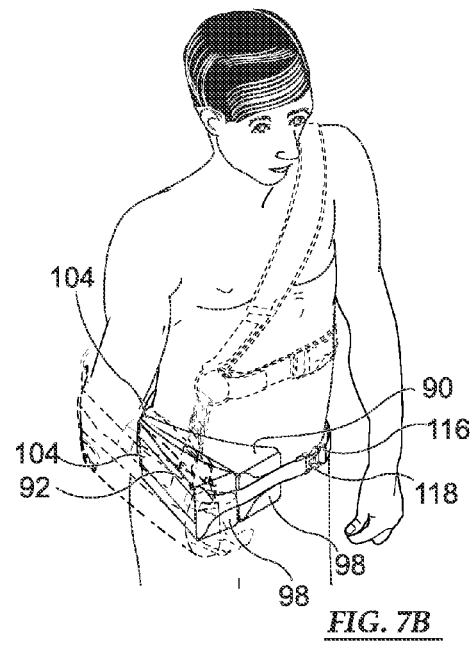
Figure 8A:
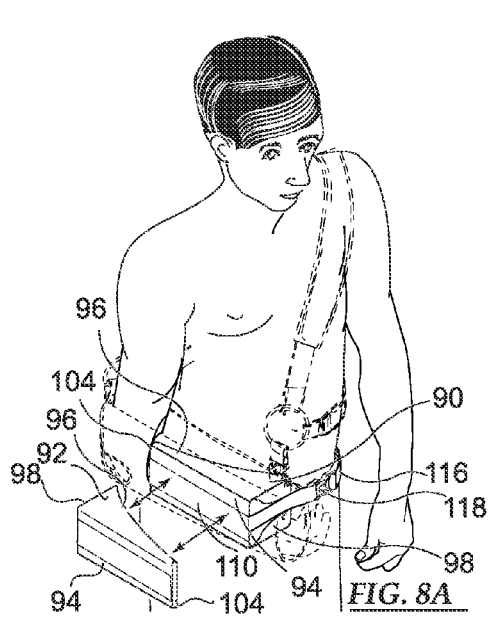
FIGS. 8A and 8B show a method for mounting the shoulder orthosis, which includes an alternate configuration of the pillow system of FIG. 5, on a patient to maintain the shoulder in a 15° abduction treatment position.
Figure 8B:
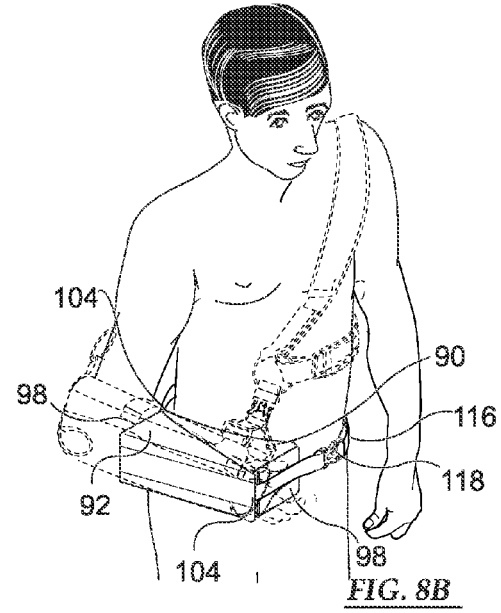

Still another method for mounting the shoulder orthosis 10, which includes an alternate configuration of the shoulder positioning pillow system of FIGS. 7A and 7B, is described below with reference to FIGS. 8A and 8B. The present method is essentially the same as described above with reference to FIGS. 7A and 7B except that the single combined pillow is configured to maintain the affected shoulder of a patient in a 15° abduction treatment position in accordance with an embodiment of the enhanced shoulder abduction configuration. The present enhanced shoulder abduction configuration of the combined pillow is assembled by positioning pillow 92 to the outside of pillow 90 with vertical face 98 of pillow 90 positioned adjacent vertical edge 104 of pillow 92 and edge 104 of pillow 90 positioned adjacent vertical face 98 of pillow 92. Vertical face 96 of pillow 92 is pressed against vertical face 94 of pillow 90 causing fastener 112 of pillow 92 to engage fastener 110 of pillow 90 and maintain the instant combined pillow configuration. Waist belt 114 is maintained assembled on pillow 90 and fitted in substantially the same manner as described above with respect to the single individual shoulder positioning pillow shown in FIG. 6D.

Vertical face 96 of pillow 90 is positioned in engagement with the patient's anterior torso at or near the waist with edge 104 of pillow 90 and vertical face 98 of pillow 92 directed posteriorly and vertical face 98 of pillow 90 and edge 104 of pillow 92 directed anteriorly. Vertical face 94 of pillow 92 is positioned in engagement with arm retainer 12 and is releasably fastened to lateral side 34 by means of fasteners 110 and 42, respectively. In comparison with the single individual pillow of FIG. 6D, the instant combined pillow configuration does not significantly increase the overall horizontal pillow width at the segment corresponding to edge 104 of pillow 92 and vertical face 98 of pillow 90, which is termed the anterior width dimension of the combined pillow in the enhanced shoulder abduction configuration. Furthermore, it is apparent from a comparison of FIGS. 7B and 8B that the anterior width dimension of the combined pillow in the enhanced shoulder abduction configuration is substantially less than the anterior width dimension of the combined pillow in the enhanced shoulder rotation configuration. Accordingly, by anteriorly positioning this segment of the combined pillow adjacent to the wrist, the shoulder orthosis 10 having the instant combined pillow configuration continues to impose an angular treatment position of 45° with respect to external rotation. However, the instant combined pillow configuration substantially increases the overall horizontal pillow width at the segment corresponding to vertical face 98 of pillow 92 and edge 104 of pillow 90, which is termed the posterior width dimension of the combined pillow in the enhanced shoulder abduction configuration. Furthermore, it is apparent from a comparison of FIGS. 7B and 8B that the posterior width dimension of the combined pillow in the enhanced shoulder abduction configuration is substantially greater than the posterior width dimension of the combined pillow in the enhanced shoulder rotation configuration. Accordingly, by posteriorly positioning this segment of the combined pillow adjacent to the elbow, the shoulder orthosis 10 having the instant combined pillow in the enhanced shoulder abduction configuration displaces the elbow outward away from the torso, thereby imposing an angular treatment position of 15° on the shoulder with respect to abduction.

There are other embodiments of a shoulder orthosis not shown which are readily within the purview of one of ordinary skill in the art following the teaching herein and are within the scope of the present invention. Such embodiments may employ the above-described modular multi-pillow system in combination with any conventional arm support known in the art which includes an arm retainer and a supportive strapping system. For example, it is within the scope of the present invention to substitute all or part of the strapping system and arm retainer (termed a forearm wrap) disclosed in U.S. Pat. No. 7,244,239 for the above-described supportive strapping system and arm retainer 12. An exemplary alternate strapping system is a single continuous adjustable over-the-shoulder support strap anteriorly connected to the front of the arm retainer and posteriorly connected to the back of the arm retainer, thereby obviating connector 26. Another exemplary alternate strapping system is one or more support straps which encircle the torso in whole or in part and additionally loop around or otherwise engage the forearm, thereby also functioning as an arm retainer.

The present invention also contemplates alternate embodiments of the modular multi-pillow system having multiple (i.e., two or more) individual pillows which are not shown, but are readily within the purview of one of ordinary skill in the art following the teaching herein. A common feature of the specific embodiments of the modular multi-pillow system described above and of alternate modular multi-pillow systems not shown, but also within the scope of the present invention, is that at least one individual pillow of a modular multi-pillow system of the present invention has two or more faces, each of which can be inwardly oriented (with reference to the resulting single combined pillow) to align with, engage and releasably attach to a corresponding attachment face of another individual pillow of the system. The resulting releasably attached pillows in combination form the combined pillow which is positionable as an arm spacer between the arm retainer, intervening forearm and torso of the user to maintain the shoulder in a desired treatment position. The user can readily modify the treatment position effected by the modular multi-pillow system simply by withdrawing the combined pillow from between the forearm and torso, detaching the individual pillows from one another, reorienting the faces of at least one of the pillows so that an alternate face of that pillow is aligned with the corresponding attachment face of the other pillow (or another attachment face of the other pillow), releasably reattaching the individual pillows to one another at the aligned faces and reinserting the resulting combined pillow between the forearm and torso to maintain the shoulder in a new desired treatment position.

It is further apparent that the specific shoulder treatment positions described above are merely exemplary. Any number of shoulder treatment positions are attainable by employing different embodiments of the modular multi-pillow system of the present invention and/or by reconfiguring the orientation of the individual pillows within a given embodiment of the modular multi-pillow system of the present invention to achieve an alternate shape of the resulting combined pillow. In any case, it is preferable that the faces of at least one individual pillow of a modular multi-pillow system define an irregular shape for the individual pillow. An "irregular shape", as the term is used herein, refers to a shape which is other than a parallelogram and, more preferably, which is asymmetrical. As such, it is noted that the wedge shape of individual pillows 90, 92 constitutes an irregular shape. By providing the modular multi-pillow system with at least one individual pillow having an irregular shape, the user is able to achieve alternate shapes of the resulting combined pillow simply by reorienting the irregularly-shaped individual pillow with respect to the at least one other individual pillow of the modular multi-pillow system so that a different face of the irregularly-shaped pillow aligns with and releasably attaches to the attachment face of the other individual pillow.

While the forgoing preferred embodiments of the invention have been described and shown, it is understood that alternatives and modifications, such as those suggested and others, may be made thereto and fall within the scope of the invention.

I claim:

1. A shoulder orthosis comprising:
a pliant forearm sleeve;
at least one support strap supporting said forearm sleeve; and
a combined pillow having a sleeve engagement face engaging said forearm sleeve and a wearer engagement face engagable with an arcuate body surface on an anterior torso of a wearer, wherein said wearer engagement face is contoured in substantial correspondence with the arcuate body surface, said combined pillow comprises a first pillow and a second pillow releasably engaging said first pillow, said combined pillow has an enhanced shoulder rotation configuration having a first pillow alignment and an enhanced shoulder abduction configuration having a different second pillow alignment, and said combined pillow is transitionable from said enhanced shoulder rotation configuration to said enhanced shoulder abduction configuration by disengaging said first and second pillows in said first pillow alignment, realigning said first and second pillows in said second pillow alignment and reengaging said first and second pillows in said second pillow alignment, and
wherein said first pillow has a wedge shape with a tapered end, a widened end, a vertical second pillow engagement face extending between said tapered end of said first pillow and said widened end of said first pillow and a vertical outside face on an opposite side of said first pillow from said vertical second pillow engagement face and likewise extending between said tapered end of said first pillow and said widened end of said first pillow, further wherein said vertical outside face of said first pillow is said wearer engagement face of said combined pillow and has an arcuate contour, and further wherein said vertical second pillow engagement face has a first end at said widened end of said first pillow and a second end at said tapered end of said first pillow;
wherein said second pillow has a wedge shape with a tapered end, a widened end, a vertical first pillow engagement face extending between said tapered end of said second pillow and said widened end of said second pillow and a vertical outside face on an opposite side of said second pillow from said vertical first pillow engagement face and likewise extending between said tapered end of said second pillow and said widened end of said second pillow, further wherein said vertical outside face of said second pillow is said sleeve engagement face of said combined pillow, and further wherein said vertical first pillow engagement face has a first end at said widened end of said second pillow and a second end at said tapered end of said second pillow;
wherein said vertical second pillow engagement face of said first pillow is engaged with said vertical first pillow engagement face of said second pillow and said first end of said first pillow is adjacent to said first end of said second pillow in said first pillow alignment, thereby resulting in said enhanced shoulder rotation configuration; and
wherein said vertical second pillow engagement face of said first pillow is engaged with said vertical first pillow engagement face of said second pillow and said first end of said first pillow is adjacent to said second end of said second pillow in said second pillow alignment, thereby resulting in said enhanced shoulder abduction configuration.

2. The shoulder orthosis of claim 1, wherein said vertical second pillow engagement face of said first pillow is releasably attached to said vertical first pillow engagement face of said second pillow when said combined pillow is in said enhanced shoulder rotation configuration and in said enhanced shoulder abduction configuration.

3. The shoulder orthosis of claim 1, wherein said combined pillow is substantially a triangular prism in said enhanced shoulder rotation configuration and said combined pillow is substantially a solid rectangle in said enhanced shoulder abduction configuration.

4. The shoulder orthosis of claim 1, wherein said combined pillow has an anterior width dimension and a posterior width dimension, and wherein said posterior width dimension is substantially less than said anterior width dimension in said enhanced shoulder rotation configuration.

5. The shoulder orthosis of claim 4, wherein said anterior width dimension of said combined pillow is substantially equal to said posterior width dimension of said combined pillow in said enhanced shoulder abduction configuration, further wherein said anterior width dimension of said combined pillow in said enhanced shoulder abduction configuration is substantially less than said anterior width dimension of said combined pillow in said enhanced shoulder rotation configuration, and further wherein said posterior width dimension of said combined pillow in said enhanced shoulder abduction configuration is substantially greater than said posterior width dimension of said combined pillow in said enhanced shoulder rotation configuration.

6. The shoulder orthosis of claim 1, wherein said vertical first pillow engagement face of said second pillow has an arcuate contour and said first pillow and said second pillow have a same configuration.

7. A shoulder orthosis comprising:
a pliant forearm sleeve;
at least one support strap supporting said forearm sleeve; and
a combined pillow having a sleeve engagement face engaging said forearm sleeve and a wearer engagement face engagable with an arcuate body surface on an anterior torso of a wearer, wherein said wearer engagement face is contoured in substantial correspondence with the arcuate body surface, said combined pillow comprises a first pillow and a second pillow releasably engaging said first pillow, said first pillow includes said wearer engagement face of said combined pillow and said second pillow includes said sleeve engagement face of said combined pillow, said combined pillow has an enhanced shoulder rotation configuration having a first pillow alignment and an enhanced shoulder abduction configuration having a different second pillow alignment, and said combined pillow is transitionable from said enhanced shoulder rotation configuration to said enhanced shoulder abduction configuration by disengaging said first and second pillows in said first pillow alignment, realigning said first and second pillows in said second pillow alignment and reengaging said first and second pillows in said second pillow alignment, and wherein said first pillow has a wedge shape with a tapered end and a widened end and has a vertical first edge at said tapered end and a vertical second edge and a vertical third edge at said widened end;

wherein said second pillow has a wedge shape with a tapered end and a widened end and has a vertical first edge at said tapered end and a vertical second edge and a vertical third edge at said widened end;

wherein said first pillow and said second pillow are positioned in engagement with one another such that said vertical first edge of said first pillow is positioned adjacent to said vertical first edge of said second pillow in said first pillow alignment, thereby resulting in said enhanced shoulder rotation configuration of said combined pillow substantially having a shape of a triangular prism, and further wherein said first pillow and said second pillow are alternatively positioned in engagement with one another such that said vertical first edge of said first pillow is selectively positioned adjacent to said vertical second edge of said second pillow or said vertical third edge of said second pillow in said second pillow alignment, thereby resulting in said enhanced shoulder abduction configuration of said combined pillow substantially having a shape of a solid rectangle.

8. The shoulder orthosis of claim 7, wherein said first pillow has a vertical second pillow engagement face and said second pillow has a vertical first pillow engagement face and said vertical first and second pillow engagement faces engage one another in said combined pillow, and wherein said vertical second pillow engagement face of said first pillow has said vertical first edge of said first pillow at a first end of said vertical second pillow engagement face and has said vertical second edge or said vertical third edge of said first pillow at an opposite second end of said vertical second pillow engagement face, and wherein said vertical first pillow engagement face of said second pillow has said vertical first edge of said second pillow at a first end of said vertical first pillow engagement face and has said vertical second edge or said vertical third edge of said second pillow at an opposite second end of said vertical first pillow engagement face.

9. The shoulder orthosis of claim 8, wherein said first pillow has a vertical outside face on an opposite side of said first pillow from said vertical second pillow engagement face, wherein said vertical outside face likewise has said vertical first edge of said second pillow at a first end of said vertical outside face and has said vertical second edge or said vertical third edge of said second pillow at an opposite second end of said vertical outside face, and further wherein said vertical outside face of said first pillow is said wearer engagement face of said combined pillow and has an arcuate contour.

10. The shoulder orthosis of claim 8, wherein said second pillow has a vertical outside face on an opposite side of said second pillow from said vertical first pillow engagement face, wherein said vertical outside face likewise has said vertical first edge of said second pillow at a first end of said vertical outside face and has said vertical second edge or said vertical third edge of said second pillow at an opposite second end of said vertical outside face, and further wherein said vertical outside face of said second pillow is said sleeve engagement face of said combined pillow.

11. A shoulder orthosis comprising:
a pliant forearm sleeve engaging a forearm of a wearer;
at least one support strap supporting said forearm sleeve; and
a combined pillow having a sleeve engagement face is adapted to engage said forearm sleeve and a wearer engagement face engagable with an arcuate body surface on an anterior torso of a wearer, wherein said wearer engagement face is contoured in substantial correspondence with the arcuate body surface, said combined pillow comprises a first pillow and a second pillow releasably engaging said first pillow, said first pillow includes said wearer engagement face of said combined pillow and said second pillow includes said sleeve engagement face of said combined pillow, and said first pillow has a plurality of vertical faces and said second pillow has a plurality of vertical faces, further wherein said combined pillow is positionable between the forearm and the anterior torso of the wearer with said forearm sleeve positioned laterally adjacent to one of said plurality of vertical faces of said second pillow, further wherein another one of said plurality of said vertical faces of said first pillow is positioned in engagement with one of said plurality of vertical faces of said second pillow resulting in an enhanced shoulder rotation configuration substantially having a shape of a triangular prism, and further wherein said another one of said plurality of said vertical faces of said first pillow is positioned in engagement with said one of said plurality of vertical faces of said second pillow resulting in an enhanced shoulder abduction configuration substantially having a shape of a solid rectangle.

12. The shoulder orthosis of claim 11, wherein said first pillow has a wedge shape with a tapered end and a widened end and said second pillow has a wedge shape with a tapered end and a widened end, and wherein said tapered end of said first pillow is positioned adjacent to said tapered end of said second pillow when said combined pillow is in said enhanced shoulder rotation configuration.

13. The shoulder orthosis of claim 12, wherein said first pillow has a vertical outside face extending between said tapered and widened ends of said first pillow and said vertical outside face of said first pillow is said wearer engagement face of said combined pillow and has an arcuate contour, and further wherein said second pillow has a vertical outside face extending between said tapered and widened ends of said second pillow and said vertical outside face of said second pillow is said sleeve engagement face.

14. The shoulder orthosis of claim 11, wherein said first pillow has a wedge shape with a tapered end and a widened end and said second pillow has a wedge shape with a tapered end and a widened end, and wherein said widened end of said first pillow is positioned adjacent to said widened end of said second pillow when said combined pillow is in said enhanced shoulder rotation configuration.

15. The shoulder orthosis of claim 11, wherein said first pillow has a wedge shape with a tapered end and a widened end and said second pillow has a wedge shape with a tapered end and a widened end, and wherein said tapered end of said first pillow is positioned adjacent to said widened end of said second pillow when said combined pillow is in said enhanced shoulder abduction configuration.

16. The shoulder orthosis of claim 11, wherein said first pillow has a wedge shape with a tapered end and a widened end and said second pillow has a wedge shape with a tapered end and a widened end, and wherein said widened end of said first pillow is positioned adjacent to said tapered end of said second pillow when said combined pillow is in said enhanced shoulder abduction configuration.

17. The shoulder orthosis of claim 11, wherein said combined pillow in said enhanced shoulder abduction configuration is adapted to maintain a shoulder at an external rotation angle of about 45° and an abduction angle greater than 0°.

18. The shoulder orthosis of claim 11, wherein said combined pillow in said enhanced shoulder abduction configuration is adapted to increase an abduction angle of a shoulder associated with the forearm of the wearer and decrease an external rotation angle of the shoulder relative to said combined pillow in said enhanced shoulder rotation configuration.

19. The shoulder orthosis of claim 11, wherein said combined pillow in said enhanced shoulder rotation configuration is adapted to maintain a shoulder at an external rotation angle of about 90° and an abduction angle of about 0°.

* * * * *